United States Patent
Petschen et al.

(10) Patent No.: US 7,626,038 B2
(45) Date of Patent: Dec. 1, 2009

(54) METHOD FOR MANUFACTURING ENANTIOMERIC IMIDAZOLE COMPOUNDS

(75) Inventors: Inés Petschen, Barcelona (ES); Xavier Camps, Barcelona (ES); Juan Sallarés, Sant Cugat (ES)

(73) Assignee: Ferrer Internacional, S.A., Barcelona (ES)

( * ) Notice: Subject to any disclaimer, the term of this patent is extended or adjusted under 35 U.S.C. 154(b) by 342 days.

(21) Appl. No.: 11/662,255

(22) PCT Filed: Sep. 13, 2005

(86) PCT No.: PCT/EP2005/009824

§ 371 (c)(1),
(2), (4) Date: Jun. 7, 2007

(87) PCT Pub. No.: WO2006/029811

PCT Pub. Date: Mar. 23, 2006

(65) Prior Publication Data

US 2008/0108682 A1    May 8, 2008

(30) Foreign Application Priority Data

Sep. 13, 2004  (ES) ................................ 200402184

(51) Int. Cl.
*C07D 233/54* (2006.01)
*C07D 409/12* (2006.01)

(52) U.S. Cl. ............... 548/311.4; 548/300.1; 548/311.1
(58) Field of Classification Search ............... 548/311.4
See application file for complete search history.

(56) References Cited

U.S. PATENT DOCUMENTS

| 5,135,943 | A | * | 8/1992 | Foguet et al. | ............... 514/397 |
| 5,939,555 | A | * | 8/1999 | Foguet et al. | ............ 548/311.1 |
| 7,323,433 | B2 | * | 1/2008 | Foguet et al. | ............... 504/275 |

FOREIGN PATENT DOCUMENTS

| CN | 1 358 719 A | 7/2002 |
| EP | 0 151 477 B1 | 8/1985 |
| GB | 2 025 395 A | 1/1980 |
| JP | 57-169466 A | 10/1982 |
| WO | WO-03/068770 A | 8/2003 |

OTHER PUBLICATIONS

Raga M M et al., Arzneimittel Forschung, Drug Research, ECV Editio Cantor Verlag, Aulendorf, DE, vol. 42, No. 5A, 1992, pp. 691-694.

* cited by examiner

*Primary Examiner*—Golam M Shameem
(74) *Attorney, Agent, or Firm*—Birch, Stewart, Koalsch & Birch, LLP

(57) ABSTRACT

The invention relates to a method for manufacturing R-(−)-sertaconazole mononitrate. The invention also relates to R-(−)-sertaconazole mononitrate hemiacetonate.

27 Claims, 1 Drawing Sheet

METHOD FOR MANUFACTURING ENANTIOMERIC IMIDAZOLE COMPOUNDS

FIELD OF THE INVENTION

Figure 1:
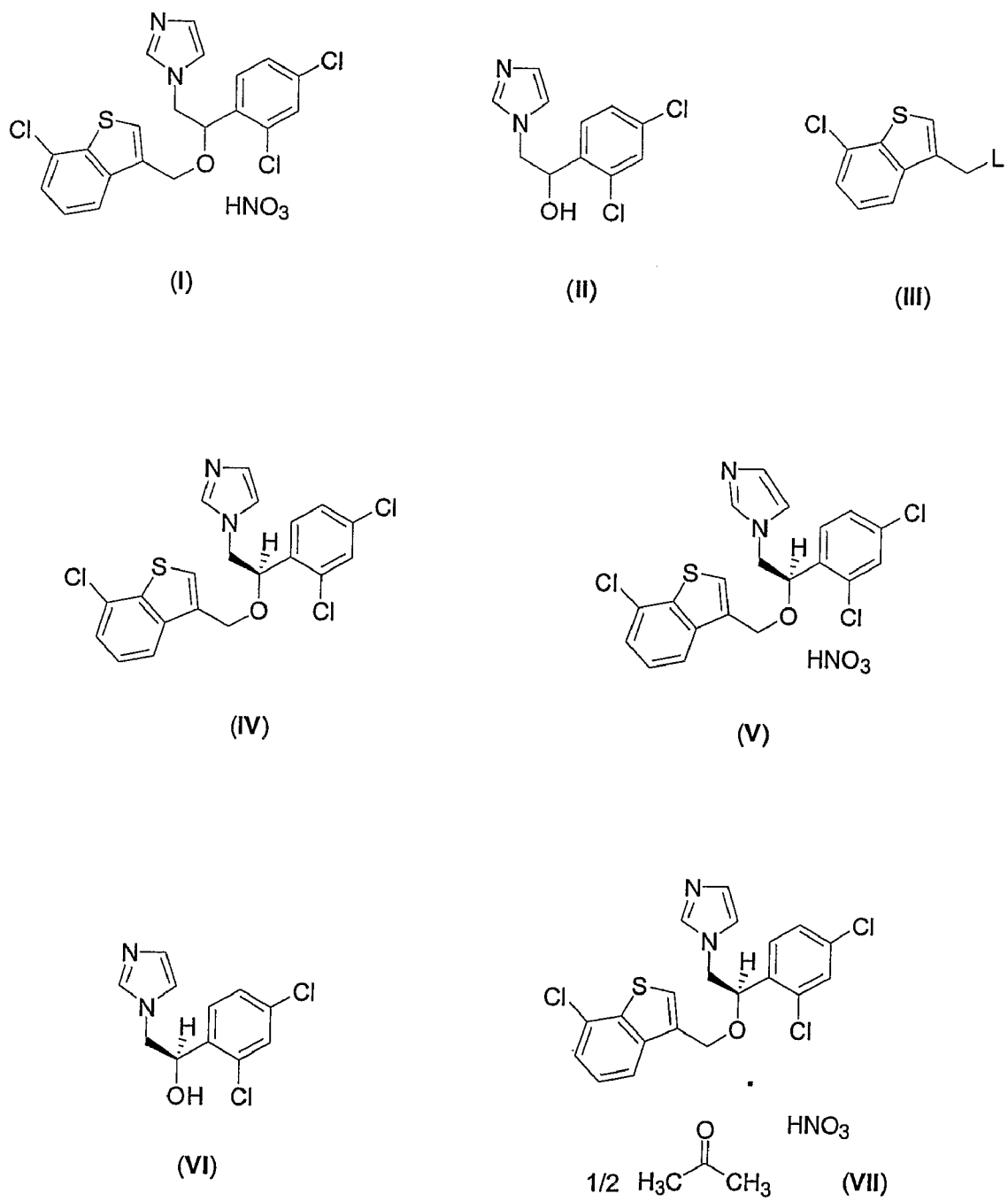

The present invention relates to a method for manufacturing enantiomeric imidazole compounds comprising R-sertaconazole, and salts and solvates thereof.

BRIEF DESCRIPTION OF ILLUSTRATIONS

FIG. 1 shows the formulas of compounds (I)-(VII).

BACKGROUND OF THE INVENTION

Sertaconazole (INN-WHO) is an antifungal agent broadly used in the therapy of infections caused by fungi and yeasts in man an animals. Sertaconazole is 1-[2-(7-chlorobenzo[b]thiopheno-3-ylmethoxy)-2-(2,4-dichlorophenyl)ethyl]-1H-imidazole. Commonly sertaconazole is used as mononitrate salt (I).

EP 151477, which is merely cited as an illustration, discloses the preparation of sertaconazole mononitrate (I) by reacting 1-(2,4-dichlorophenyl)-2-(1H-imidazol-1-yl)ethanol (II) with sodium hydride and 3-bromomethyl-7-chlorobenzo[b]thiophene (III, L=Br) in hexamethylphosphoramide and treating the resulting sertaconazole free base with nitric acid.

Applicants have discovered that out of the two potential enantiomers of sertaconazole, the antifungal activity mainly lies in the R-(-)-enantiomer. It is, therefore, of a great interest to develop improved methods for manufacturing R-(-)-sertaconazole (IV) and its derived salts. R-(-)-sertaconazole (IV) and its preferred salt, the mononitrate (V), have been disclosed in WO 03068770. R-(-)-sertaconazole (IV) and R-(-)-sertaconazole mononitrate (V) are potent antifungal agents for medicinal, veterinary and agricultural use.

WO 03068770 discloses the preparation of R-(-)-sertaconazole (IV) by reacting R-(-)-1-(2,4-dichlorophenyl)-2-(1H-imidazol-1-yl)-ethanol (VI) with 3-(chloromethyl or bromomethyl)-7-chlorobenzo[b]thiophene (III, L=Cl, Br) in N,N-dimethylformamide and in the presence of potassium t-butoxide as a base. The yield of this operation is only 25%. Thereafter, the mononitrate salt (V) is obtained by acidifying with nitric acid in a mixture of ethanol and water (yield=89%). Overall yield of the process is then 22% only.

DESCRIPTION

The present invention provides a new chemical process for the preparation of R-(-)-sertaconazole mononitrate (V).

More specifically, the present invention provides a phase-transfer process for manufacturing R-(-)-sertaconazole mononitrate (V), which is more advantageous than the process described in WO 03068770. In contrast to the latter, the process of this invention avoids the use of column chromatography, which is a hardly operational procedure because it is slow and costly and requires large amounts of solvent. In addition, the process of this invention provides an unexpected higher yield and leads to a product having the appropriate characteristics for its use in the preparation of pharmaceutical, veterinary and agricultural compositions. Although the process of the present invention comprises basic but modified elements from prior art, its industrial use in compliance with current environmental, economical and technological requirements can be satisfactorily accomplished.

The present invention provides a method for manufacturing R-(-)-sertaconazole mononitrate (V) comprising the phase-transfer reaction of R-(-)-1-(2,4-dichlorophenyl)-2-(1H-imidazol-1-yl)-ethanol (VI):

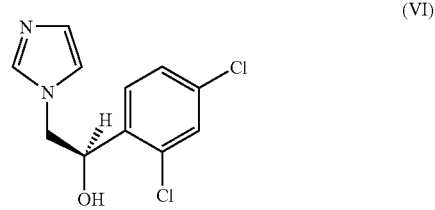

(VI)

with an intermediate of general formula (III):

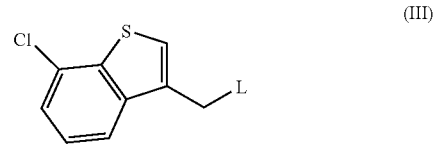

(III)

wherein L is a leaving group, in the presence of a phase-transfer catalyst and a base, followed by treatment with nitric acid.

In another embodiment of the present invention, the phase-transfer catalyst is usually a quaternary nitrogen, phosphorus or sulfur salt and the like. Alternatively, crown ethers, cryptates, soluble polyethyleneglycol polymers and the like may also be employed. Among the quaternary salts, the nitrogen salts are preferred. The quaternary nitrogen salts comprise a cation derived from a tertiary amine or a cation derived from an amine, whose nitrogen atom is a part of an aromatic ring, and a conventional anion. Particularly preferred examples of cations derived from tertiary or aromatic amides are benzyltributylammonium, benzyltriethylammonium, cetylpyridinium, cetyltrimethylammonium, hexadecyltriethylammonium, hexadecyltrimethylammonium, methyltrioctylammonium, N-benzylquininium, octyltrimethylammonium, tetrabutylammonium, tetraethylammonium, tetramethylammonium, tricaprylylmethylammonium and the like. Tetrabutylammonium is preferably used. Particularly preferred examples of conventional anions are acid sulfate, chloride, bromide, fluoride, hydroxyl, nitrate, iodide, phosphate, acetate, benzoate, salicylate, methanesulfonate, p-toluenesulfonate, L-lactate, and the like. Acid sulfate and chloride and preferably used.

In another embodiment of the present invention, the phase-transfer reaction is carried out in a medium containing an immiscible solvent in water and water. As immiscible solvents in water, hydrocarbons, either aromatic or aliphatic, and chlorinated aliphatic hydrocarbons. In a non-limitative manner, toluene, xylenes, cyclohexane, hexane, heptane, octane, nonane, dichloromethane and their admixtures may be employed. Toluene is preferably used.

In another embodiment of the present invention, R-(-)-sertaconazole mononitrate (V), thus obtained, is purified either by recrystallization from a solvent or admixture of appropriate solvents or by precipitation of the product dissolved on a solvent in which it is insoluble.

In another embodiment of the present invention, the recrystallization of R-(-)-sertaconazole mononitrate (V) is carried out in an alcohol having one to four carbon atoms or in an admixture composed of an alcohol having one to four carbon atoms and in a second solvent selected from an acetone having one to four carbon atoms, an ester having one to five carbon atoms and an aromatic hydrocarbon having one to eight carbon atoms.

In another embodiment of the present invention, the recrystallization of R-(−)-sertaconazole mononitrate (V) is carried out in an admixture of acetone and ethanol or acetone and methanol. The admixture of acetone and ethanol is preferred. The solid thus obtained is R-(−)-sertaconazole mononitrate with ½ mol of acetone, which can also be termed R-(−)-sertaconazole mononitrate hemiacetonate (VII), and the product being very pure.

Other embodiment of the present invention is that by drying at a temperature range of 80-90° C., intermediate (VII) loses the salvation acetone and is converted again into R-(−)-sertaconazole mononitrate (V), but having a higher purity.

Other embodiment of the present invention is that the drying temperature of intermediate (VII) is 85° C.

In a another embodiment of the present invention, R-(−)-sertaconazole mononitrate (V), thus obtained, is finally purified again by recrystallization in an admixture consisting of an alcohol having one to four carbon atoms and water. End product, R-(−)-sertaconazole mononitrate (V), is obtained with an appropriate quality to be used in pharmaceutical, veterinary and agricultural compositions.

In the present invention, pharmaceutical compositions imply those preparations intended for humans by either topical use, such as bath additives, creams, gels, ointments, cutaneous pastes, medicated plasters, cutaneous foams, shampoos, solutions for cutaneous sprays, suspensions for cutaneous sprays, powders for cutaneous sprays, cutaneous liquids, cutaneous solutions, cutaneous suspensions, cutaneous emulsions, cutaneous powders, transdermal patches, collodions, medicated nail lacquers, poultices, cutaneous sticks, cutaneous sponges, impregnated dressings, and the like; or vaginal use, such as vaginal creams, vaginal gels, vaginal ointments, vaginal foams, vaginal solutions, vaginal suspensions, vaginal emulsions, tablets for vaginal solution, pessaries, hard vaginal capsules, soft vaginal capsules, vaginal tablets, effervescent vaginal tablets, medicated vaginal tampons, vaginal delivery systems, and the like; or by oromucosal administration, such as gargles, concentrates for gargles, powders for gargle solutions, tablets for gargle solutions, oromucosal solutions, oromucosal suspensions, oromucosal drops, oromucosal sprays, sublingual sprays, mouth washes, tablets for mouth wash solutions, gingival solutions, oromucosal gels, oromucosal pastes, gingival gels, gingival pastes, sublingual tablets, muco-adhesive buccal tablets, buccal tablets, lozenges, compressed lozenges, pastilles, an the like; or by dental use, such as dental gels, dental sticks, dental inserts, dental powders, dental solutions, dental suspensions, dental emulsions, toothpastes, and the like.

In the present invention, veterinary compositions imply those preparations intended for pets by either topical use, such as collars, medicated pendants, ear tags, dip solutions, dip suspensions, dip emulsions, concentrates for dip solutions, concentrates for dip suspensions, concentrates for dip emulsions, pour-on solutions, pour-on suspensions, pour-on emulsions, spot-on solutions, spot-on-suspensions, spot-on emulsions and the like; or vaginal use, such as vaginal sponges and the like.

In the present invention, agricultural compositions imply those preparations intended to improve crops, such as either the preparations to be added to the irrigation water or the preparations to be sprayed or sprinkled on the plants. Other dosage forms for agricultural use, such as powders, creams, pastes and the like, can be formulated Other embodiment of the present invention is that the leaving group L of the compound of general formula (III) is selected from a halogen atom (for example, chlorine, bromine or iodine), a sulfonate group (for example p-toluenesulfonate, brosylate, nosylate, methanesulfonate, triflate, nonaflate, tresylate and the like), an acyloxy group (preferably saturated or unsaturated having one to eight carbon atoms, such as a group represented by R—C(=O)—O— wherein R is an aryl group optionally substituted by alkyl (preferably having six to eight carbon atoms, such as the phenyl and p-tolyl group and the like)), an aryloxy group optionally substituted by alkyl (preferably having six to eight carbon atoms, such as the phenoxy and p-tolyloxy group and the like), an aralkyl group (preferably having seven to nine carbon atoms, such as the benzyl group and the like), an arylalkenyl group (preferably having eight or nine carbon atoms, such as the cynamyl group and the like), an aralkyloxy group (having seven to fifteen carbon atoms, such as the benzyloxy and 9-fluorenylmethoxy group and the like), or an alkoxy group (linear or branched having one to eight carbon atoms, such as methoxy, ethoxy, t-butoxy and the like), and the like. Chlorine, bromine and iodine atoms, p-toluenesulfonate, brosylate, nosylate, methanesulfonate, triflate, nonaflate, tresylate, alkylcarbonate, phenylcarbonate groups and the saturated and unsaturated acyloxy groups and the like are preferred; Chlorine and bromine atoms and p-toluenesulfonate and methanesulfonate groups are particularly preferred.

Another embodiment of the invention is that the tetrabutylammonium salt used in the phase-transfer reaction is selected from the group consisting of acid sulfate, chloride, bromide, fluoride, hydroxyl, nitrate, iodide, phosphate, acetate, benzoate, salicylate, methanesulfonate, p-toluenesulfonate, L-lactate, and the like.

Another embodiment of the invention is that the tetrabutylammonium salt used in the phase-transfer reaction is selected from either tetrabutylammonium acid sulfate or tetrabutylammonium chloride.

Another embodiment of the invention is that the base used in the phase-transfer reaction is selected from the group consisting of hydroxide, carbonate or alkaline or alkaline earth metal bicarbonate.

Another embodiment of the invention is that the base used in the phase-transfer reaction is sodium hydroxide, potassium hydroxide, potassium carbonate, sodium carbonate and sodium carbonate.

Another embodiment of the invention is that the base used in the phase-transfer reaction is selected from either sodium hydroxide and potassium hydroxide.

Another embodiment of the present invention concerns intermediate R-(−)-sertaconazole mononitrate hemiacetonate (VII).

The present invention will now be described in detail by the following non-limiting examples.

EXAMPLE 1

R-(−)-1-(2,4-dichlorophenyl)-2-(1H-imidazol-1-yl)-ethanol (VI)

To a solution of 5 g of 1-(2,4-dichlorophenyl)-2-(1H-imidazol-1-yl)-ethanol (II) in a mixture of acetone-methanol, 3.21 g of D-tartaric acid dissolved in a mixture of acetone-methanol were added at room temperature. Once the addition was completed, the mixture was stirred for further 30 minutes at room temperature. The resultant solid was filtered and crystallized from methanol. A mixture consisting of the resulting salt, water and methylene chloride was treated with a concentrated solution of sodium hydroxide. The organic layer was washed with water and concentrated at reduced pressure to yield 1.85 g (37%) of (VI) whose enantiomeric purity was higher than 98% in R-(−) isomer.

EXAMPLE 2

R-(−)-Sertaconazole mononitrate (V)

a) Preparation of R-(−)-sertaconazole mononitrate hemiacetonate (VII)

A 10-L flask was loaded with 1.54 L of toluene, 500 g of R-(−)-1-(2,4-dichlorophenyl)-2-(1H-imidazol-1-yl)-ethanol (VI) (1.94 mol) and 33.5 g of tetrabutylammonium acid sulfate (X) (0.0987 mol). Then, 775 g of 49% NaOH (9.51 mol) were slowly added. The mixture was heated at 35-40° C. and stirred for further 15 minutes and then a solution of 555 g of 3-bromomethyl-7-chlorobenzo[b]thiophene (III, L=Br) (2.122 mol) and 3.4 L of toluene was added in the course of 30 minutes at a mass temperature of 37-40° C. After the addition, the system was maintained between 37 and 40° C. for 2.5 hours and thereafter 3.16 L of water were added. The mixture was decanted and the organic layer was washed twice with 0.865 L of water. The solvent was distilled under reduced pressure. The crude product obtained was dissolved in 2.5 L of ethanol and a solution of 290 g of 60% nitric acid (2.76 mol) in 1 L of water was added and then cooled to a temperature between −5 and 5° C. for 1 hour. The solid formed was filtered and washed with water. A 10-L flask was loaded with the solid obtained in the preceding operation, which was recrystallized from a mixture of acetone-ethanol to give R-(−)-sertaconazole mononitrate solvate with ½ mol of acetone (VII).

| Crystallographic properties of R-(—)-sertaconazole mononitrate hemiacetonate (VII) | |
|---|---|
| Empirical formula | $C_{20}H_{16}Cl_3N_3O_4S \cdot 0.5\ C_3H_6O$ |
| Molecular weight | 529.82 |
| Wavelength (Å) | 0.71069 |
| Crystal system, space group | Monoclinical, $P2_1$ |
| Unit cell dimensions (Å) = | 15.3710(10) |
| b = | 9.7800(10) |
| c = | 17.5570(10) |
| β (°) = | 92.7800(10) |
| Volume (Å$^3$) | 2636.2(4) |
| Z, calculated density (Mg/m$^3$) | 4, 1.287 |
| μ (mm$^{-1}$) | 0.534 |
| F(000) | 512 |
| Crystal size (mm) | 0.1 × 0.1 × 0.2 |
| Theta range for data collection | 1.3-28.5 gr. |
| Index ranges | $0 \leq h \leq 18, 0 \leq k \leq 12,$ $-22 \leq l \leq 21$ |
| Collected/Independent reflections | 5644/5033 [R(int) = 0.03] |
| Totalization rate at 2 Θ | 87.4% |
| Data/parameters | 5033/596 |
| Goodness-of-fit on F$^2$ | 1.98 |
| Final R Indices [l > 2sigma(l)] | R1 = 0.1001, wR2 = 0.301 |
| Absolute structure parameter | −0.02(10) |
| Largest diff. peak and hole | 0.38 and −0.47 e.A$^{-3}$ | b) Preparation of R-(−)-sertaconazole mononitrate (V)

R-(−)-sertaconazole mononitrate hemiacetonate (VII), as obtained in the preceding stage (a), was washed with acetone and dried at 85° C. in order to remove the acetone from the solvate. 758 g of R-(−)-sertaconazole mononitrate (V) were obtained (Yield=77.8%).

c) Purification of R-(−)-sertaconazole mononitrate (V)

R-(−)-sertaconazole mononitrate (V), as obtained in the preceding stage (b), was recrystallized from a mixture of ethanol-water (2:1) and cooled from reflux temperature to −5/5° C. in he course of 2-4 hours. The solid obtained was dried at 60° C. and micronized. 689 g of R-sertaconazole mononitrate were obtained (Overall yield=70.8%).

The invention claimed is:

1. A method for manufacturing R-(−)-sertaconazole mononitrate (V) which comprises:

a) the reaction of R-(−)-1-(2,4-dichlorophenyl)-2-(1H-imidazol-1-yl)-ethanol (VI):

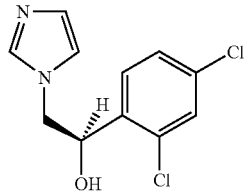

(VI)

with an intermediate of general formula (III):

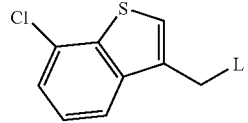

(III)

wherein L is a leaving group, in the presence of phase-transfer catalyst in a medium constituted by an immiscible solvent in water and water, and in the presence of a base, followed by treatment with nitric acid and recrystallization of the solid formed from an appropriate solvent;

b) the conversion of the solid formed in the preceding stage into R-(−)-sertaconazole mononitrate (V) by drying at a temperature between 80 and 90° C.; and c) the purification of R-(−)-sertaconazole mononitrate (V) obtained in the preceding stage.

2. The method according to claim 1, wherein the leaving group, represented by L, is selected from the group consisting of chlorine atom, bromine atom, iodine atom, p-toluenesulfonate group, brosylate group, nosylate group, methanesulfonate group, triflate group, nonaflate group, tresylate group, alkylcarbonate group, phenylcarbonate group, saturated acyloxy group and unsaturated acyloxy group.

3. The method according to claim 1, wherein the leaving group, represented by L, is selected from the group consisting of chlorine atom, bromine atom, p-toluenesulfonate group and methanesulfonate group.

4. The method according to claim 1, wherein the phase-transfer catalyst is a quaternary nitrogen, phosphorus or sulfur salt.

5. The method according to claim 4, wherein the quaternary salt is quaternary nitrogen salt.

6. The method according to claim 5, wherein the quaternary nitrogen salt comprises a tertiary amine cation or an amine cation whose nitrogen atom is a part of an aromatic ring, and an anion.

7. The method according to claim 6, wherein the quaternary nitrogen salt comprises a tertiary amine cation and an anion.

8. The method according to claim 7, wherein the cation is selected from the group consisting of benzyltributylammonium, benzyltriethylammonium, cetyltrimethylammonium, hexadecyltriethylammonium, hexadecyl-trimethylammonium, methyltrioctylammonium, N-benzylquininium, octyltrimethylammonium, tetrabutyl-ammonium, tetraethylammonium, tetramethylammonium, and tricaprylylmethylammonium.

9. The method according to claim 8, wherein the cation is tetrabutylammonium.

10. The method according to claim 7, wherein the anion is selected from the group consisting of acid sulfate, chloride, bromide, fluoride, hydroxyl, nitrate, iodide, phosphate, acetate, benzoate, salicylate, methanesulfonate, p-toluenesulfonate, and L-lactate.

11. The method according to claim 10, wherein the anion is either acid sulfate or chloride.

12. The method according to any one of claims 7, 9 and 11, wherein the quaternary salt is either tetrabutylammonium acid sulfate or tetrabutylammonium chloride.

13. The method according to claim 1, wherein the immiscible solvent in water is selected from the group consisting of aromatic hydrocarbons, aliphatic hydrocarbons, chlorinated aliphatic hydrocarbons and mixtures thereof.

14. The method according to claim 13, wherein the immiscible solvent in water is selected from the group consisting of toluene, xylene, cyclohexane, hexane, heptane, octane, nonane, dichloromethane, dichloroethane and mixtures thereof.

15. The method according to claim 14, wherein the immiscible solvent in water is toluene.

16. The method according to claim 1, wherein the base used in the phase-transfer reaction is selected from the group consisting of an alkaline metal hydroxide, alkaline-earth metal hydroxide, carbonate and bicarbonate.

17. The method according to claim 16, wherein the base used in the phase-transfer reaction is selected from the group consisting of sodium hydroxide, potassium hydroxide, sodium carbonate, potassium carbonate and sodium bicarbonate.

18. The method according to claim 17, wherein the base used in the phase-transfer reaction is either sodium hydroxide or potassium hydroxide.

19. The method according to claim 1, wherein the appropriate solvent is an alcohol having one to four carbon atoms or a mixture of an alcohol having one to four carbon atoms and a second solvent selected from the group consisting of an acetone having one to four carbon atoms, an ester having one to five carbon atoms and an aromatic hydrocarbon having one to eight carbon atoms.

20. The method according to claim 19, wherein the appropriate solvent is a mixture of an alcohol having one to four carbon atoms and an acetone having one to four carbon atoms.

21. The method according to claim 20, wherein the appropriate solvent is a mixture of ethanol and acetone.

22. The method according to claim 1 or 21, wherein the solid formed is R-(−)-sertaconazole mononitrate hemiacetonate (VII).

23. The method according to claim 1, wherein the drying temperature is 85° C.

24. The method according to claim 1, wherein the purification comprises a recrystallization from a mixture of an alcohol having one to four carbon atoms and water.

25. The method according to claim 24, wherein the alcohol is ethanol.

26. The method according to any one of claims 24 and 25, said method comprising in addition a micronization step.

27. R-(−)-sertaconazole mononitrate hemiacetonate (VII).

* * * * *